United States Patent

Stormbom

[11] Patent Number: 5,619,144
[45] Date of Patent: Apr. 8, 1997

[54] DETECTOR AND METHOD FOR OBSERVATION OF THE PRESENCE OF A LIQUID AND/OR OF A CHANGE OF PHASE IN SAME

[75] Inventor: Lars Stormbom, Vantaa, Finland

[73] Assignee: Vaisala Oy, Vantaa, Finland

[21] Appl. No.: 294,565

[22] Filed: Aug. 23, 1994

[30] Foreign Application Priority Data

Aug. 23, 1993 [FI] Finland ................................. 933701

[51] Int. Cl.$^6$ ............................ G01N 27/06; G01R 27/22
[52] U.S. Cl. ........................... 324/694; 324/441; 324/443; 324/706
[58] Field of Search ................................ 324/441, 443, 324/693, 694, 706

[56] References Cited

U.S. PATENT DOCUMENTS

| | | | |
|---|---|---|---|
| 4,135,151 | 1/1979 | Rogers et al. | 324/693 |
| 4,333,004 | 6/1982 | Forgue et al. | 219/497 |
| 4,335,613 | 6/1982 | Luukkala | 73/599 |
| 4,378,168 | 3/1983 | Kuisma et al. | 374/28 |
| 4,523,142 | 6/1985 | Murata et al. | 324/693 |
| 4,808,009 | 2/1989 | Sittler et al. | 374/178 |
| 4,897,597 | 1/1990 | Whitener | 324/693 |
| 4,942,364 | 7/1990 | Nishijima et al. | 324/696 |
| 4,996,493 | 2/1991 | Monat et al. | 324/699 |

FOREIGN PATENT DOCUMENTS

| | | |
|---|---|---|
| 376721 | 4/1990 | European Pat. Off. . |
| 60079 | 7/1981 | Finland . |
| 61249 | 2/1982 | Finland . |
| A1800345 | 3/1993 | Finland . |
| B92440 | 7/1994 | Finland . |
| 3924634 | 1/1991 | Germany . |
| 068658 | 4/1984 | Japan . |

*Primary Examiner*—Kenneth A. Wieder
*Assistant Examiner*—Glenn W. Brown
*Attorney, Agent, or Firm*—Jones & Askew

[57] ABSTRACT

Detector and method for detecting the presence of a liquid, such as water dew or of ice, or for detecting a change of phase in liquid, based on a change in an electrical resistance. The detector comprises a substrate onto whose face one or several resistor patterns are applied. For detecting the presence of a liquid or ice or equivalent by a change in the detector resistance, a low-mass detector resistor pattern is applied onto a substrate out of such a metal or equivalent as has a considerable dependence on temperature. On the substrate, there are contact patterns that feed a short pulse of electric current to heat the detector resistor as a short pulse, the presence of a liquid or ice and or a change of phase being detected by the change in resistance taking place during the short pulse. The thickness of the metal film in the resistor pattern (15) of the detector resistor ($R_{det}$) is, as a rule, chosen as s<1 μm.

14 Claims, 2 Drawing Sheets

DETECTOR AND METHOD FOR OBSERVATION OF THE PRESENCE OF A LIQUID AND/OR OF A CHANGE OF PHASE IN SAME

The invention concerns a detector for detecting the presence of a liquid, in particular of water dew and/or of ice, and/or for detecting a change of phase in the liquid, which detector is based on a change in the electrical resistance and which detector comprises a substrate, onto whose face one or several resistor patterns have been applied.

Further, the invention concerns a method based on observation of a change in the electrical resistance for detecting the presence of a liquid, in particular of water dew and/or of ice, and/or for detecting a change of phase in the liquid.

In particular, the invention concerns a detector and a method intended for detecting the presence of a liquid and in particular of dew. Detectors for the presence of a liquid, in particular of water dew, are needed, for example, in various electronic apparatuses, in automobile windshields, in various measurement apparatuses, such as hygrometers. As is known from the prior art, a dew-point detector has also been used for measurement of relative humidity by detecting the temperature at which dew starts condensing on the face of the detector.

As is known from the prior art, the detectors used for detection of dew have been based on a change in the reflectivity of the active face of the detector, on measurement of the changes in the dielectric or electric properties of a hygroscopic material, or on measurement of the mass of the condensed water. Some examples of the prior art related to the present invention are the applicant's FI Patents Nos. 60,079 and 61,249 (corresponding U.S. Pat. Nos. 4,378,168 and 4,335,613).

The general object of the present invention is further development of the prior art. It is a particular object of the invention to provide a detector which has a simple construction and a favourable process of manufacture as well as which is of a rapid and reliable operation.

In view of achieving the objectives stated above and those that will come out later, the detector of the invention is mainly characterized in that, in view of detecting the presence of a liquid or ice or equivalent on the basis of a change in the detector resistance, a low-mass detector resistor pattern has been applied onto a substrate out of such a metal or equivalent as has a considerable dependence on temperature, and that on said substrate there are contact patterns, by whose means an electric current that heats the detector resistor can be fed into the detector resistor as a short pulse, the presence of a liquid or ice and/or a change of phase in same being detectable on the basis of the change in resistance taking place during said short pulse.

On the other hand, the method in accordance with the invention is mainly characterized in that the detector resistor, which is placed in the area of observation and whose resistance changes as a function of the temperature, is heated by means of electric current in short-time periods, and that the phenomenon to be monitored is detected on the basis of the change in the detector resistance taking place during said periods or on the basis of an electrical quantity derived from said change.

Since the thermal mass of the active part of the detector in accordance with the invention has been made very little, its temperature is restored substantially to the temperature of the environment quite rapidly, typically in a few seconds. Thus, by means of a detector in accordance with the invention, the measurements can be repeated at intervals of a few seconds, being timed by the system of measurement.

The detector in accordance with the invention is of simple construction and of economical technique of manufacture. The detectors in accordance with the invention can be manufactured by means of methods in themselves known so that their properties become as of high homogeneity.

In the following, the invention will be described in detail with reference to an exemplifying embodiment of the invention illustrated in the figures in the accompanying drawing, the invention being by no means strictly confined to the details of said embodiment.

Figure 1:
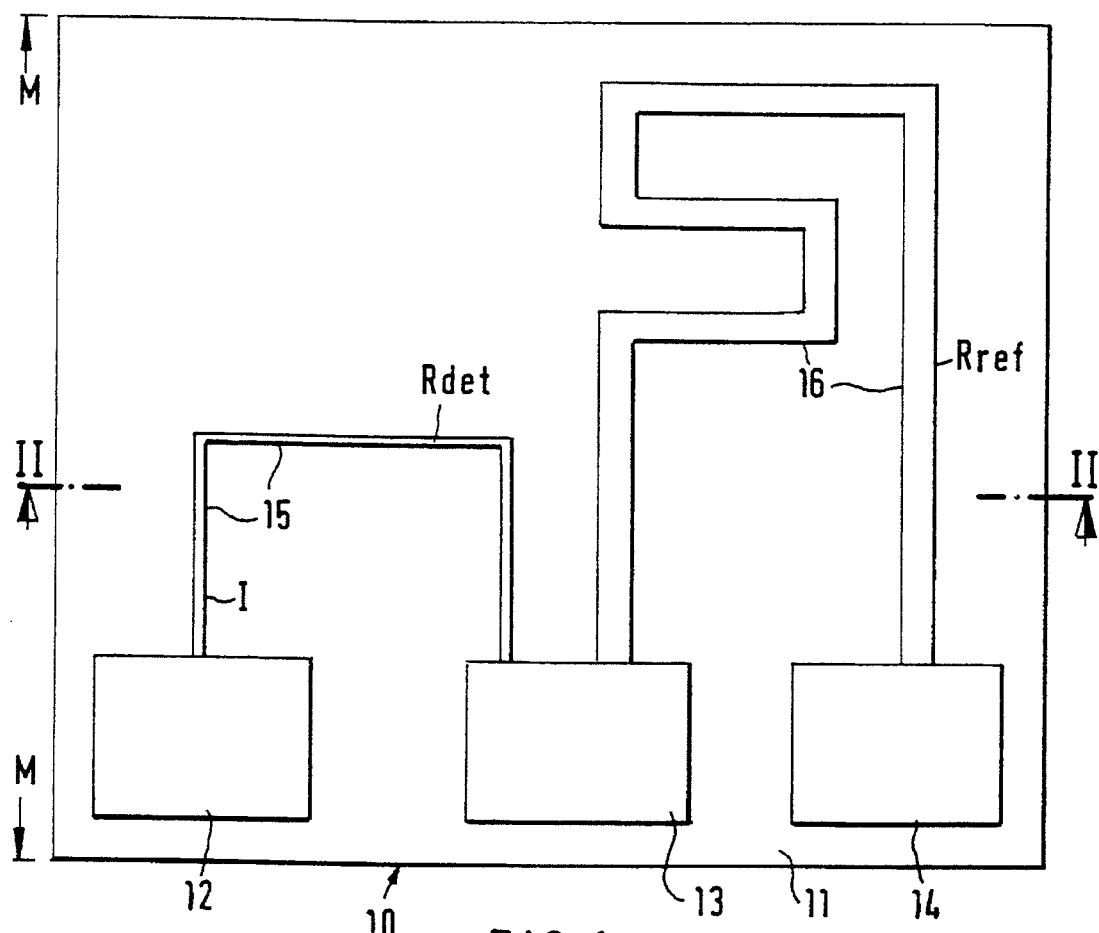
FIG. 1 shows a detector in accordance with the invention viewed from above.
Figure 2:
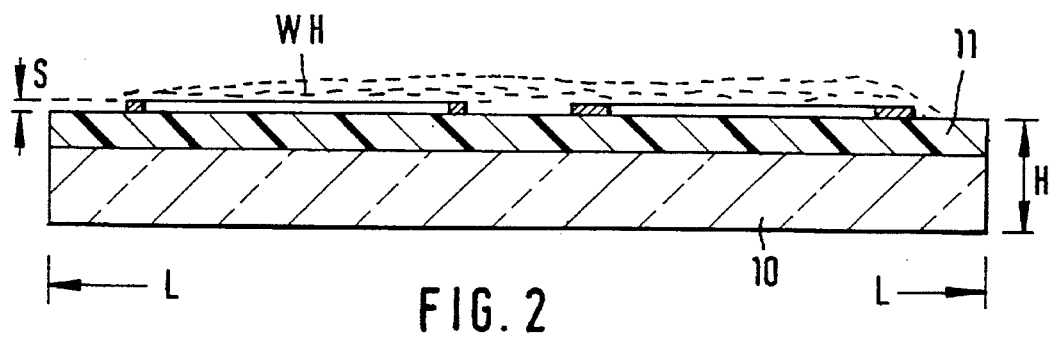
FIG. 2 is a sectional view taken along the line II—II in FIG. 1.

The detector shown in FIGS. 1 and 2, which is particularly well suitable for detecting the presence of water dew, comprises a plane robust substrate 10, whose thermal capacity is relatively low. The substrate is made of plastic or glass. The dimensions L×M×H of the substrate 10 are typically 3 mm×3 mm×0.2 mm. As is shown in FIG. 2, onto the face of the substrate, a thin plastic film 11 has been fixed, in which case the substrate 10 may be a base otherwise poorly suitable for a substrate, for example a structural part of some device, which may be even made of an electrically conductive material. Onto the outer face of the film 11, two resistor patterns 15 and 16 have been applied, which patterns are electrically connected to the contact patterns 12, 13 and 14, of which the middle contact pattern 13 is common of both of the resistor patterns 15 and 16. The resistor patterns 15,16 and the contact patterns 12,13,14 are preferably made by means of the thin-film technique. The thickness s of the resistor patterns 15 and 16 is very little, as a rule, always s<1 μm. It is an essential feature of the invention that the thermal mass of the resistor pattern 15, which operates as the detector resistor $R_{det}$, is very little, which is always the case when s<1 μm. The metal or the equivalent conductive material in the resistor patterns 15 and 16 must have a considerable dependence on temperature, which dependence may be either positive or negative. Particularly suitable metals for the resistor patterns 15,16 as well as for the contact patterns 12,13 and 14 are gold, platinum or palladium.

The resistor pattern 15 forms the active resistance $R_{det}$ of the detector and, in a corresponding way, the resistor pattern 16, which is not needed necessarily in all applications, forms a reference resistance $R_{ref}$.

In the method of the invention, the detector described above is placed in the area of observation, and the detector resistor $R_{det}$ is heated by the intermediate of the contact patterns 12 and 13 by means of electric current I in short periods $t_0$. Based on the change taking place in the detector resistance $R_{det}$ during the heating periods $t_0$ or on some other electric quantity derived from said change, the phenomenon to be monitored is detected in a way that will be described in more detail later.

When electric current I is fed into the resistor pattern 15 made of a metal layer, the temperature of the metal in said pattern rises rapidly because of the very low thermal mass of the structure. Since the conductivity of the metal in the resistor pattern 15 has a considerable dependence on temperature, this heating produces a change in the detector resistance $R_{det}$ in the resistor pattern 15, which change is detected. If dew WH or some other liquid or ice has condensed onto and around the face of the resistor pattern 15, the change in the resistance $R_{det}$ becomes significantly slower because of the thermal mass of the water and because of the energy required by the evaporation or melting of said water. When the detector resistor $R_{det}$ is heated with a substantially invariable electric power $W=I^2R_{det}$, it is possible to detect the presence, and in some cases even the quantity, of the dew and/or ice as the time taken by the change in resistance $\Delta R_{ref}$ corresponding to a certain change in the temperature, as the rate of change in the resistance, or as a change in the resistance after a certain time of heating, or in some other, corresponding way.

The metal layer in the resistor pattern 15 is preferably made porous, whereby it is possible to increase the face of contact of the water with the metal and thereby to increase the effect of dew on the change in the speed of increase in the temperature. Since the thermal mass of the detector structure is very little, its temperature is restored substantially to the temperature of the environment very rapidly, typically in a few seconds. Thus, the measurement can be repeated at intervals of a few seconds.

The length of the periods $t_0$ of heating of the detector resistor $R_{det}$, which are repeated at intervals of a few seconds, is, as a rule, in the range of $t_0 \approx 0.1$ ms . . . 5 ms. In the construction as shown in FIGS. 1 and 2, preferably $t_0 \approx 1$ ms . . . 2 ms. In the method of the invention, one significant quantity is the energy of the heating pulse $V_0$ per area of the detector resistor $R_{det}$, which quantity is, as a rule, chosen in the range of 1 . . . 20 mJ/mm$^2$, preferably in the range of 3 . . . 10 mJ/mm$^2$. In this connection, the length of the detector resistor $R_{det}$ means the length measured in the plane of the face of the substrate 10 of the resistor pattern 15, and the width means the width measured in the same plane perpendicularly to said length. The heating power W is typically in the range of $W \approx 1$ . . . 10 W, and the detector resistance $R_{det}$ is typically in the range of $R_{det} \approx 10$ Ω . . . 1 kΩ, so that the heating current I is in the range of $I \approx 30$ mA . . . 1 A. The values given above are given expressly for use in a detector as shown in FIGS. 1 and 2, and in detectors of a different sort, which are also included in the scope of the invention, they may differ considerably from those given above.

Figure 3:
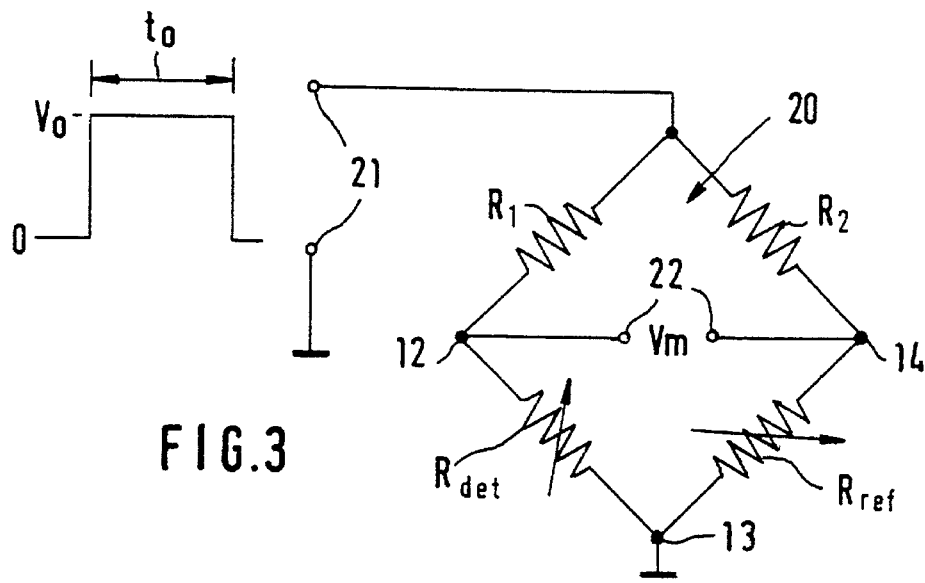
FIG. 3 shows an application of a detector in accordance with the invention in connection with an electric bridge construction.

FIG. 3 shows a bridge construction 20, by whose means the change in the value of the detector resistance $R_{det}$ during heating can be expressed directly as a voltage $V_m$, which is measured from the terminals 22 of the bridge. In the bridge construction 20, there may be an adjustable separate reference resistor $R_{ref}$, which is not heated significantly during measurement. If the detector must operate in a wide range of temperatures, the separate adjustable resistor $R_{ref}$ is, as is shown in FIGS. 1 and 2, substituted for by a reference resistor $R_{ref}$ made of the same metal as the detector resistor $R_{det}$, said reference resistor consisting of the resistor pattern 16 shown in FIG. 1. In such a case, the magnitude of the reference resistance $R_{ref}$ is, when a voltage pulse $V_0$ is fed into it through the terminals 21 of the bridge, at the beginning of the pulse, substantially the same as the value of the detector resistance $R_{det}$. The area of the reference resistor $R_{ref}$ has been dimensioned substantially larger than the area of the detector resistor $R_{det}$, so that the reference resistor is not heated significantly during the voltage pulse $V_0$. In such a case, the bridge construction 20 remains at the equilibrium across a wide temperature range. In a way in itself known, the bridge construction of FIG. 3 includes invariable resistors $R_1$ and $R_2$, which are preferably as invariable as possible irrespective of any changes in temperature.

Figure 4:
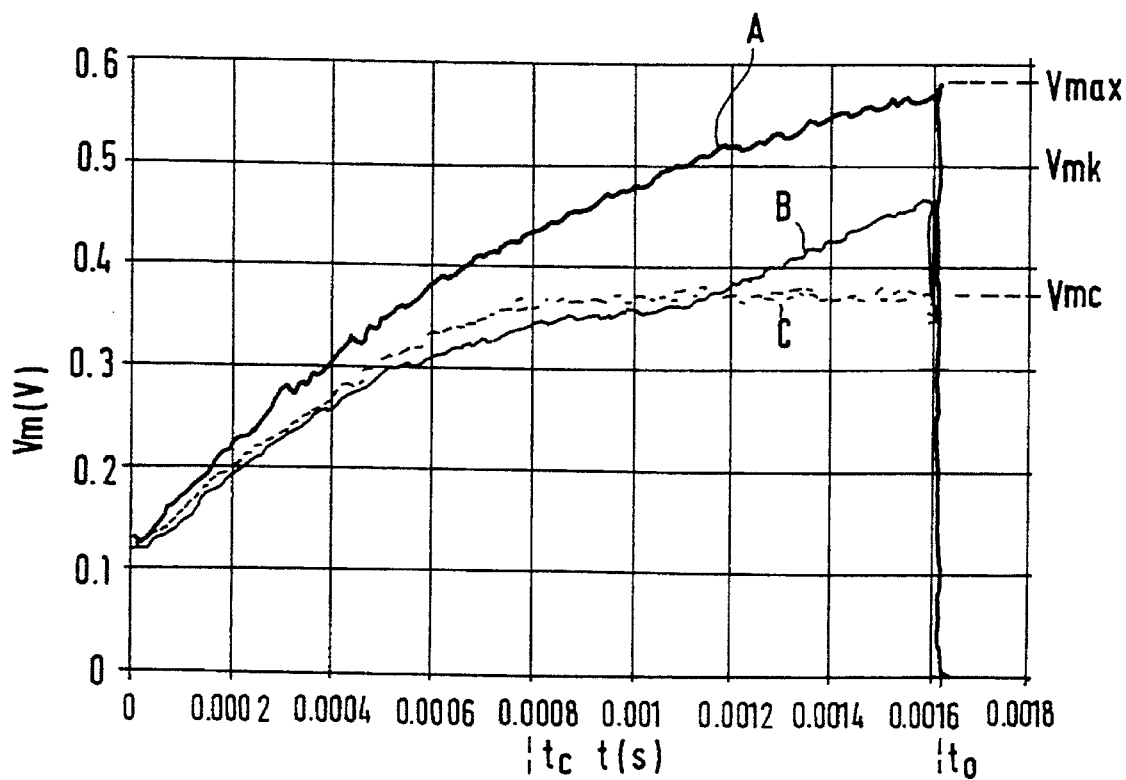
FIG. 4 illustrates output voltages obtained from a bridge construction as shown in FIG. 3 in different operating environments of the detector.

FIG. 4 shows the voltage $V_m$ changes during the heating period $t_0$, measured from a bridge construction 20 as shown in FIG. 3 by means of a detector as shown in FIGS. 1 and 2. To the terminals 21 of the bridge 20, a rectangular voltage pulse $V_0=0$ . . . 30 V is fed, whose duration is $t_0=1.6$ ms. The curve A in FIG. 4 represents the voltage increase curve of a dry detector during the heating period $t_0$, during which the voltage rises from about 0.1 V to about 0.6 V. In a corresponding way, the curve B represents the voltage $V_m$ increase during the period $t_0$ in a situation in which there is a thin dew layer WH on the detector face. In such a case, the voltage rises by about 0.45 V, i.e. clearly more slowly than with the dry detector (curve A). In a corresponding way, the curve C represents the voltage $V_m$ increase when there is a thick dew layer WH on the active face of the detector in connection with the detector resistor $R_{det}$. According to the curve C, during the time period $t_c$ . . . $t_0$, the voltage $V_m$ is substantially invariable $V_{mc}=0.37$ V, which illustrates the situation that the detector resistor $R_{det}$ has been heated so intensively that its temperature exceeds the water boiling point, i.e. a phase change takes place in the condensed water WH, for which reason the voltage $V_m$ remains invariable, $=V_{mc}$, during the period of time $t_c$ . . . $t_0$. There is a corresponding invariable area of the voltage $V_m$ if there is ice on the face of the detector, in which case, when the ice melts and the phase is changed, the voltage $V_m$ remains invariable. On this phenomenon, it is possible to base the use of the detector in accordance with the present invention also as a detector of the presence of ice, for example, on roads and in different vehicles, such as automobiles and airplanes. The circumstance is also based on the phenomenon described above that there is quite a great difference between the maximal voltage $V_{max}$ of a dry detector and the voltage $V_{mc}$ of a moist detector, which situation makes the detection reliable.

In FIG. 4, the reference $V_{mk}$ denotes a threshold voltage, and when $V_m(t_0)>V_{mk}$, the system to which said detector and said bridge construction 20 belong indicates that there is no liquid or ice, and when $V_m(t_0)>V_{mk}$, the system indicates the presence of dew or ice. By means of the detector in accordance with the invention, the change in phase can be detected thereby that the voltage $V_m$ remains substantially invariable ($V_{mc}$) during a period of time that is longer than a certain threshold time in the heating period $t_0$.

A change in the detector resistance $R_{det}$ can also be detected electrically so that the voltage that is fed to the detector resistor is kept invariable with a sufficiently high precision and the current that passes through the detector resistor $R_{det}$ or the rate of change in said current is measured. In a corresponding way, the current flowing through the detector resistor $R_{det}$ can be kept invariable while the voltage occurring between the contact patterns 12 and 13 at the terminals of the detector resistor is measured. Said current I and/or the voltage between the terminals 12,13 can be changed during the heating periods $t_0$ at a suitable preset and known rate.

In some applications, the operation of the dew-point detector in accordance with the invention can also be connected with measurement of relative humidity so that, based on the resistance of the detector resistor $R_{det}$, the temperature is determined at which the dew evaporates from the active face of the detector.

In the following, the patent claims will be given, and the various details of the invention may show variation within the scope of the inventive idea defined in said claims and differ from the details given above by way of example only.

I claim:

1. Detector for detecting the presence of water in the form of water dew or ice, which detector is based on a change in an electrical resistance and which detector comprises a substrate (10,11), onto whose face at least one resistor pattern is applied, characterized in that, for detecting the presence of water on the basis of a change in resistance of a detector resistor ($R_{det}$), a low-mass detector resistor pattern (15) is applied onto a substrate (10,11) out of a material having a characteristic substantially dependent on temperature, that on said substrate there are contact patterns (12,13) by whose means an electric current (I) that heats the detector resistor ($R_{det}$) is fed into the detector resistor ($R_{det}$) as a short pulse ($t_0$), the presence of water being detected by the change in resistance of the detector resistor ($R_{det}$) taking place during said short pulse, that the detector resistor ($R_{det}$) and a reference resistor ($R_{ref}$) are placed at different branches of a bridge connection responsive to the current pulse, and that the area of the reference resistor is substantially larger than the area of the detector resistor, so that the reference resistor is not significantly heated during the current pulse.

2. Detector as claimed in claim 1, characterized in that the thickness of a metal film in the resistor pattern (15) of the detector resistor ($R_{det}$) is s<1 μm.

3. Detector as claimed in claim 1, characterized in that a thin metal film in the pattern (15) of the detector resistor ($R_{det}$) is porous but electrically continuous.

4. Detector as claimed in claim 1, characterized in that the pattern (15) of the detector resistor ($R_{det}$) is applied onto a substrate (10, 11) made of plastic or glass.

5. Apparatus for detection of water dew, that makes use of a detector as in claim 1, characterized in that the water detector resistor ($R_{det}$) and the reference resistor ($R_{ref}$) are placed at opposite branches of the bridge connection (20) so that, based on a function of the voltage increase of the bridge connection taking place during a heating period ($t_0$), the presence of water dew is detected.

6. Detector for detecting the presence of water in the form of water dew or ice, which detector is based on a change in an electrical resistance and which detector comprises a substrate (10,11), onto whose face at least one resistor pattern is applied, characterized in that, for detecting the presence of water on the basis of a change in resistance of a detector resistor ($R_{det}$), a low-mass detector resistor pattern (15) is applied onto a substrate (10,11) out of a material having a characteristic substantially dependent on temperature, that on said substrate there are contact patterns (12,13) by whose means an electric current (I) that heats the detector resistor ($R_{det}$) is fed into the detector resistor ($R_{det}$) as a short pulse ($t_0$), the presence of water being detected by the change in resistance of the detector resistor ($R_{det}$) taking place during said short pulse and that, onto the same substrate (10, 11) onto its same face as the detector resistor pattern (15), a reference resistor pattern ($R_{ref}$) is applied, to which a heating current (I) is fed through contact patterns (13, 14).

7. Detector as claimed in claim 6, characterized in that the resistor pattern (15) of the detector resistor ($R_{det}$) and the resistor pattern (16) of the reference resistor ($R_{ref}$) are placed on the same face of the substrate (10, 11) side by side, and that one of the contact patterns (13) is common of said resistor patterns (15, 16).

8. Method based on observation of a change in the electrical resistance for detecting the presence of water in the form of dew or of ice, comprising the steps of placing in the area of observation a detector resistor ($R_{det}$) whose resistance changes as a function of the temperature, heating the detector resistor by flowing an electric current (I) through the detector resistor in short-time periods ($t_0$), and detecting the presence of water as a function of the change in resistance of the detector resistor taking place during said periods ($t_0$).

9. Method as claimed in claim 8, characterized in that, in addition to the detection of dew, based on the value of the detector resistance ($R_{det}$), the temperature is detected at which the dew evaporates from a face of the detector, whereby the relative humidity (RH) of the environment of the area of observation is determined.

10. Method as claimed in claim 8, characterized in that the duration ($t_0$) of the heating is chosen in the range of $t_0 \approx 0.1 \ldots 5$ ms.

11. Method as claimed in claim 8, characterized in that the energy of the heating pulse ($V_0$) divided by the area of the detector resistor, wherein area=length×width of the detector resistor pattern (15), is chosen in the range of $1 \ldots 20$ mJ/mm$^2$.

12. Method as claimed in claim 8, characterized in that the heating power (W) is chosen high enough so that a change of phase takes place in water or ice condensed in the area of observation.

13. Method as claimed in claim 8, characterized in that the steps of heating ($t_0$) of the detector resistor ($R_{det}$) are repeated, and the presence of water is detected after each heating step.

14. Method based on observation of a change in the electrical resistance for detecting the presence of water in the form of dew or of ice, characterized in that a detector resistor ($R_{det}$), which is placed in the area of observation and whose resistance changes as a function of the temperature, is heated by means of electric current (I) in short-time periods ($t_0$), and that the phenomenon to be monitored is detected as a function of the change in the resistance of the detector taking place during said periods ($t_0$), and that the method comprises a combination of the following steps:

(a) in the area of observation, the detector resistor ($R_{det}$) has a substantial dependence on temperature;

(b) to said detector resistor ($R_{det}$), an electric current (I) that heats said resistor is fed during a relatively short period of time ($t_0$);

(c) based on a function of the resistance ($R_{det}$) of the detector resistor, the change taking place in the detector resistance ($R_{det}$) during the heating period ($t_0$), the rate of change is detected electrically; and (d) the presence of dew or of ice in said area of observation is concluded on the basis of the observation of the preceding step (c).

* * * * *